United States Patent
Mendel-Hartvig et al.

(10) Patent No.: US 9,285,361 B2
(45) Date of Patent: Mar. 15, 2016

(54) METHOD FOR THE ANALYSIS OF CIRCULATING ANTIBODIES

(75) Inventors: Ib Mendel-Hartvig, Uppsala (SE); Christer Pettersson, Storvreta (SE); Gerd Rundström, Uppsala (SE)

(73) Assignee: JOHNSON & JOHNSON AB (SE)

( * ) Notice: Subject to any disclaimer, the term of this patent is extended or adjusted under 35 U.S.C. 154(b) by 310 days.

(21) Appl. No.: 12/497,486

(22) Filed: Jul. 2, 2009

(65) Prior Publication Data

US 2010/0009465 A1 Jan. 14, 2010

Related U.S. Application Data

(60) Provisional application No. 61/078,295, filed on Jul. 3, 2008.

(51) Int. Cl.
*G01N 33/543* (2006.01)

(52) U.S. Cl.
CPC ............................... *G01N 33/54366* (2013.01)

(58) Field of Classification Search
None
See application file for complete search history.

(56) References Cited

U.S. PATENT DOCUMENTS

| | | | |
|---|---|---|---|
| 4,275,053 A | 6/1981 | Rosenfield et al. | |
| 5,192,663 A | 3/1993 | Sinor et al. | |
| 5,759,774 A * | 6/1998 | Hackett et al. | 435/2 |
| 5,773,222 A | 6/1998 | Scott | |
| 2002/0081573 A1* | 6/2002 | Lassen et al. | 435/5 |
| 2004/0063160 A1* | 4/2004 | Lassen et al. | 435/7.2 |
| 2005/0242017 A1* | 11/2005 | Staats | 210/198.2 |
| 2006/0239859 A1* | 10/2006 | Ohman et al. | 422/100 |
| 2006/0285996 A1* | 12/2006 | Ohman et al. | 422/57 |
| 2007/0059718 A1 | 3/2007 | Toner et al. | |
| 2007/0266777 A1* | 11/2007 | Bergman et al. | 73/61.41 |
| 2009/0208920 A1* | 8/2009 | Ohman et al. | 435/2 |

FOREIGN PATENT DOCUMENTS

| | | |
|---|---|---|
| WO | WO-03/103835 A1 | 12/2003 |
| WO | WO 2004/029221 A3 | 4/2004 |
| WO | WO 2005/089082 A2 | 9/2005 |
| WO | WO 2005/118139 A1 | 12/2005 |
| WO | WO 2007/149043 A1 | 12/2007 |

OTHER PUBLICATIONS

Japanese Search Report for JP Application No. 2009-157404; mailed Oct. 30, 2012; 4 pages.
Chinese Office Action and Search Report for CN Application No. 200910163972.1; dated Jun. 6, 2014; 14 pages.
European Search Report for EP Application No. 09 163 976.5; mailed Apr. 17, 2012; 4 pages.

* cited by examiner

Primary Examiner — Chris L Chin
(74) Attorney, Agent, or Firm — Barclay Damon, LLP

(57) ABSTRACT

There is provided a method for the analysis of circulating antibodies comprising the steps:
a) providing an analysis device comprising a substrate, and provided on said substrate at least one sample addition zone, at least one retaining zone, at least one sink, and at least one flow path connecting the sample addition zone, the retaining zone and the sink, wherein the flow path is open and comprises projections substantially vertical to the surface of said substrate and having a height (H), diameter (D) and reciprocal spacing (t1, t2) such that lateral capillary flow of said sample is achieved and such that cells can flow through the projections, wherein said retaining zone comprises at least one affinity binding means to which cell structures are bound,
b) adding at least one sample to a sample addition zone, and
c) reading a result,
wherein circulating antibodies directed against cell structures are determined.

10 Claims, No Drawings

METHOD FOR THE ANALYSIS OF CIRCULATING ANTIBODIES

CROSS REFERENCE TO RELATED APPLICATIONS

This application claims the benefit under 35 USC 119(e) of prior U.S. Provisional Patent Application No. 61/078,295, filed Jul. 3, 2008, the disclosure of which is hereby incorporated by reference in its entirety.

TECHNICAL FIELD

The present invention concerns a method for the analysis circulating antibodies.

BACKGROUND

Quick, reliable, and cost effective analytical and diagnostic methods are desirable.

PCT/SE03/00919 (Åmic AB) relates to a micro fluidic system comprising a substrate and provided on said substrate there is at least one flow path comprising a plurality of micro posts protruding upwards from said substrate, the spacing between the micro posts being small enough to induce a capillary action in a liquid sample applied, so as to force said liquid to move. There is disclosed that the device can comprise a denser zone which can act as a sieve preventing for instance cells to pass. There is also disclosed an embodiment with microstructures where the shape, size and/or center-to-center distance forms a gradient so that cells and the like can be delayed or separated.

PCT/SE2005/000429 (Åmic AB) shows a device and method for the separation of a component in a liquid sample prior to the detection of an analyte in said sample, wherein a sample is added to a receiving zone on a substrate, said substrate further optionally comprising a reaction zone, a transport or incubation zone connecting the receiving and reaction zone, respectively, forming a flow path on a substrate, wherein said substrate is a non-porous substrate, and at least part of said flow path consists of areas of projections substantially vertical to the surface of said substrate, and having a height, diameter and reciprocal spacing such, that lateral capillary flow of said liquid sample in said zone is achieved, and where means for separation are provided adjacent to the zone for receiving the sample. There is disclosed an embodiment where red blood cells are removed.

PCT/SE2005/000787 (Åmic AB) concerns a device for handling liquid samples, comprising a flow path with at least one zone for receiving the sample, and a transport or incubation zone, said zones connected by or comprising a zone having projections substantially vertical to its surface, said device provided with a sink with a capacity of receiving said liquid sample, said sink comprising a zone having projections substantially vertical to its surface, and said sink being adapted to respond to an external influence regulating its capacity to receive said liquid sample. It is disclosed that the device can be used when particulate matter such as cells is to be removed from the bulk of the sample. It is stated that red blood cells can be separated without significant rupture of the cells.

PCT/US2003/030965 (The General Hospital Corporation, and GPB Scientific LLC) discloses methods for separating cells from a sample. There is disclosed the separation of cells with different properties. The devices are closed devices with an input and output channel and a lid. The device comprises arrays of obstacles that are capable of binding a population of cells.

US 2007/0059718 A1 discloses methods for detecting and concentrating biohazard analytes such as bacteria, protozoa, viral pathogens, and toxins.

There is a need for a robust and reliable method for the analysis of circulating antibodies.

SUMMARY OF THE INVENTION

One object of the present invention is to provide an improved method for the analysis of circulating antibodies.

There is provided a method for the analysis of circulating antibodies comprising the steps:

providing an analysis device comprising a substrate, and provided on said substrate at least one sample addition zone, at least one retaining zone, at least one sink, and at least one flow path connecting the sample addition zone, the retaining zone and the sink, wherein the flow path is open and comprises projections substantially vertical to the surface of said substrate and having a height (H), diameter (D) and reciprocal spacing (t1, t2) such that lateral capillary flow of said sample is achieved and such that cells can flow through the projections, wherein said retaining zone comprises at least one affinity binding means to which cell structures are bound, adding at least one sample to a sample addition zone, and reading a result, wherein circulating antibodies directed against cell structures are determined.

Further aspects and embodiments of the present invention are defined in the appended claims which are incorporated herein by reference.

By providing a substrate comprising projections in combination with a retaining zone where particles and/or cells are retained by attractive forces, several advantages are obtained.

The projections give a large surface for the substrate and the large surface of the retaining zone is an advantage because cells are bound more efficiently. The kinetics of the analysis device is improved with the combination of projections and affinity binding.

The projections in combination with the affinity binding mean provide a possibility to create a suitable flow of sample liquid in the device. This allows problems such as unwanted clogging to be avoided.

A further advantage of the present invention is that the reading of a result is easier in an open system according to the present invention. Moreover there are no problems with entrapped gases in an open system.

Another advantage of using substantially vertical projections to analyse cells is that this allows design of the projections so that the cells are handled carefully.

Definitions

Before the present device and method is described, it is to be understood that this invention is not limited to the particular configurations, method steps, and materials disclosed herein as such configurations, steps and materials may vary somewhat. It is also to be understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a", "an", and "the" include plural referents unless the context clearly dictates otherwise. Thus, for example, reference to a reaction mixture containing "an antibody" includes a mixture of two or more antibodies.

The term "about" when used in the context of numeric values denotes an interval of accuracy, familiar and acceptable to a person skilled in the art. Said interval is ±10%.

In describing and claiming the device and method, the following terminology will be used in accordance with the definitions set out herein.

As used throughout the claims and the description the wording "affinity binding means to which cells are bound" denotes an element which binds to cells by attractive forces between the binding means and the cells.

As used throughout the claims and the description the term "analysis" means the process in which at least one analyte is determined.

As used throughout the claims and the description the term "analysis device" means a device by the aid of which an analysis can be performed.

As used throughout the claims and the description the term "analyte" means a substance or chemical or biological constituent of which one or more properties are determined in an analytical procedure. An analyte or a component itself can often not not be measured, but a measurable property of the analyte can. For instance, it is possible to measure the concentration of an analyte.

As used throughout the claims and the description the term "capillary flow" means flow induced mainly by capillary force.

As used throughout the claims and the description the term "casing" means an element enclosing a part of or the entire device.

As used throughout the claims and the description the term "circulating antibody" means an antibody in solution.

As used throughout the claims and the description the term "detectable group" means any arrangement of molecules or atoms that can be detected when present on a substrate.

As used throughout the claims and the description the term "flow path" means an area on the device where flow of liquid can occur between different zones.

As used throughout the claims and the description the term "fluid connection" means a connection in which a fluid can be transported.

As used throughout the claims and the description the term "lid" means an element covering a part of or the entire device.

As used throughout the claims and the description the term "open" used in connection with capillary flow means that the system is open i.e. the system is not enclosed. Examples of an open system include a system without at lid in capillary contact with the sample liquid. In an open system a lid shall not be in capillary contact with the sample liquid, i.e. a lid shall not take part in creating the capillary force.

As used throughout the claims and the description the term "reciprocal spacing" means the distance between adjacent projections.

As used throughout the claims and the description the term "retaining zone" means a zone where at least some part of a sample is retained.

As used throughout the claims and the description the term "sample" means a mixture or a solution to be analysed.

As used throughout the claims and the description the term "sample addition zone" means a zone where a sample is added.

As used throughout the claims and the description the term "sink" means an area with the capacity of receiving liquid sample.

As used throughout the claims and the description the term "substance" means any pure chemical or biological entity or any mixture or solution comprising at least one chemical or biological entity.

DETAILED DESCRIPTION

In a first aspect there is provided a method for the analysis of circulating antibodies comprising the steps:

a) providing an analysis device comprising a substrate, and provided on said substrate at least one sample addition zone, at least one retaining zone, at least one sink, and at least one flow path connecting the sample addition zone, the retaining zone and the sink, wherein the flow path is open and comprises projections substantially vertical to the surface of said substrate and having a height (H), diameter (D) and reciprocal spacing (t1, t2) such that lateral capillary flow of said sample is achieved and such that cells can flow through the projections, wherein said retaining zone comprises at least one affinity binding means to which cell structures are bound, b) adding at least one sample to a sample addition zone, and c) reading a result, wherein circulating antibodies directed against cell structures are determined.

Reciprocal spacing (t1, t2) denotes the reciprocal spacing in x and y direction in an orthogonal coordinate system. In one embodiment all projections have the same spacing in x-direction and/or y-direction. In an alternative embodiment the projections have different spacings in the x-direction. In one embodiment the distance of the different projections in x-direction are t11, t12, t13 . . . In a further embodiment the projections have different spacings in the y-direction. In one embodiment the distance of the different projections in y-direction are t21, t22, t23. . .

The device comprises a substrate. In one embodiment the substrate is partly or entirely enclosed by a casing or a lid. If a casing or a lid is used, the distance between the substrate is such that the casing or lid does not contribute to the capillary force acting on the sample liquid.

There is at least one sample addition zone to which sample liquid is added. There is a flow path in fluid connection with the sample addition zone and the retaining zone and the sink.

In one embodiment the sample flows in a flow path from a sample addition zone via a retaining zone to a sink.

In one embodiment the retaining zone is placed across the entire path/paths where the sample fluid flows so that no sample liquid is able to pass by the retaining zone. In an alternative embodiment the retaining zone is placed so that a part of the sample liquid passes the retaining zone without any essential interaction with the retaining zone.

In one embodiment at least one of a) the sample addition zone, b) the retaining zone and c) the sink, comprises projections substantially vertical to the surface of said substrate and having a height (H), diameter (D) and reciprocal spacing (t1, t2) such that lateral capillary flow of said sample is achieved and such that cells can flow through the projections.

In one embodiment the height, diameter and reciprocal spacing of the a) flow path, b) the sample addition zone, c) the retaining zone, and d) the sink are the same. In an alternative embodiment the height, diameter and reciprocal spacing of at least one of a) flow path, b) the sample addition zone, c) the retaining zone, and d) the sink are different.

In one embodiment the affinity binding means is selected from an antibody, an aptamer, a receptor, a ligand, a single chain antibody, a fragmented antibody, and a lectin.

In one embodiment the micro posts are arranged with micro post distances of 5-200 μm. In another embodiment the micro post distances is 20-100 μm.

In one embodiment the micro posts are arranged with micro post heights of 1-1000 μm. In another embodiment the micro posts height is 10-100 μm.

In one embodiment the liquid sample is selected from the group consisting of human or animal blood, urine, lung liquids, synovial fluid, wound liquids, saliva, tears, and sweat.

In one embodiment the liquid sample is from human blood.

In one embodiment the cell structures are part of the haematological antigen system.

In one embodiment the cell structures are part of the antigens involved in HIV infection or detection.

In one embodiment the liquid sample is from human blood and is used for the determination of circulating antibodies directed against bacteria, viruses or small sized single or multi cell infectious agents.

In one embodiment the liquid sample is from human bone marrow.

Other features and uses of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

Example 1

Adherence of cells to the an analyse device according to the invention.

The projections of the chip had different centre to centre spacing with the largest spacing in the flow direction. The projections were narrowing towards the top. The height of the projections was 65 μm. The diameter of the projections at the bottom was 70 μm and the diameter at the top was 50 μm. The spacing between the projections were t1=t2=31.77 μm at the bottom of the projections and t1=t2=51.77 μm at the top of the projections.

The principle of adherence of cells to the device surface is exemplified by firm binding of red blood cells (RBC). RBCs was firmly attached during free flow to a defined area of the chip surface by means of different principles including RBC agglutinins, charge and antibodies directed to surface antigens.

Small amounts (0.1 μl) of lectins 1 mg/ml in 50 mM Na-phosphate buffer, pH 7.5 were applied in a single lane on the chip where after 20 μl RBCs 0.8% in suspension were applied and let to flow through the detection zone containing the lectins. The results showed a variable RBC binding to different lectins (PHA—E, PHA—M, WGA, Jacalin) with WGA as the most efficient one. The bound RBCs that are clearly visible by eye remained attached after washing with 50 μl of buffers containing e.g. 0.1% of the detergent Tween 20. Bound RBCs was determined quantitatively by adding 10 μl of rabbit anti-human RBC in combination with 10 μl of Cy5 goat anti-rabbit IgG.

A firm binding of RBC to the chip surface was also obtained using antibodies against RBC surface antigens such as glycophorin, a major surface protein of the human RBC.

Polylysine of high molecular weight which generally bind cells firmly in cell cultures was also able to bind RBC in numbers comparable to WGA.

Attachment of RBC to the 4castchip was also possible using biotin labelled RBC in combination with deposited streptavidin. Streptavidin (0.13 μl of 2 mg streptavidin/ml) in PBS pH 7,5 was applied in a single lane on the chip. 20 μl of RBCs 1.6% labelled with Biotin using Sulfo-NHS-biotin was let to flow through the detections zone containing the streptavidin. The results showed a clearly visible firm binding of RBC to the streptavidin and remained attached after washing with 80 μl of buffers containing e.g. 0.1% of the detergent Tween 20.

Example 2

Detection of soluble human antibodies directed to RBC surface antigens (indirect antiglobin test, IAT).

The principle of antibody detection is exemplified with detection of anti-D antibodies present in low titre in human serum. The assay principle involves firm adherence or binding of viable RBCs on the chip surface by means of deposited catching e.g. antibodies against RBC surface antigens. The same device as in example 1 was used. Thus, RBCs that are transported by free flow through the micro pillars of the chip are captured by chip bound antibodies located in the detection zone. A small volume (10 μl) of a human serum samples diluted 1:100 in LISS buffer containing 0.5% gelatine containing anti-D antibodies of different titres was applied to sensitize the RBCs. Following washing (30 μl) the presence of IgG on the RBC surface was detected using 10 μl of an anti-human globulin antibody (AHG) conjugated with transfluosphere. The results showed a dose dependent binding of AHG conjugate to RBCs with respect to the anti-D antibody titre. Optimal sensitization was obtained in the absence of detergent and using low-ionic-strength saline (LISS) washing buffer containing 0,5% gelatine.

In the high sensitivity IAT assay the detection with the AHG-conjugate is done with fluorescent dye combinations with extremely large stoke shift (the separation between excitation and emission maxima) like in the Transfluosphere and europium conjugates.

Example 3

ABO Blood Group Antigen Testing

The ABO blood group antigens on RBCs are determined with high specificity. RBCs from donor blood samples were prepared by washing twice in LISS buffer and then re-suspended to a 0.8% RBC solution. The washed donor RBCs (4%, 20 μl) in LISS buffer were attached to the device using deposited anti-glycophorin (1 mg/ml, 0.13 μl/chip). The A- and B-antigens respectively were detected using 10 μl of monoclonal anti- RBC-A and RBC-B antibodies followed by 10 μl of an anti-mouse IgM antibody conjugated with Cy5. The chip was finally washed with 60 μl of an assaybuffer (20 mM Tris, 0.135 M NaCl, 10 mM EDTA, 0.1% Tween 20, 1% BSA, pH 7.4). The fluorescence signal read at 635 nm was clearly positive for A positive RBCs and negative (equal to background signal) for B positive RBCs using anti-RBC-A antibodies. The same high specificity was obtained in experiments with B positive RBCs.

The invention claimed is:
1. A method for the analysis of circulating antibodies, said method comprising the steps of:
 a. providing an analysis device comprising a substrate, and provided on said substrate at least one sample addition zone, at least one retaining zone, at least one sink, and at least one flow path connecting the at least one sample addition zone, the at least one retaining zone and the at least one sink, wherein the at least one flow path is open and comprises projections substantially vertical to the surface of said substrate and having a height (H), diameter (D) and reciprocal spacing (t1, t2) such that lateral capillary flow of at least one liquid sample is spontaneously achieved along said at least one flow path and such that cells can flow through the projections, wherein said at least one retaining zone comprises at least one affinity binding means to which cell structures are bound, b. binding cells or cell structures onto projections in said at least one retaining zone, said cells or cell structures forming binding surfaces, c. adding a liquid sample to said sample addition zone, d. binding circulating antibodies onto said formed binding surfaces, and e. reading a result, wherein circulating antibodies directed against bound cell structures are determined, in which the projections are defined by a tapered configuration and in which the projections are narrower at the top of the projections than the bottom and in which the reciprocal spacing between projections is larger between the top of adjacent projections than the bottom thereof.

2. The method according to claim 1, wherein said at least one liquid sample is selected from the group consisting of human or animal blood, urine, lung liquids, synovial fluid, wound liquids, saliva, tears, and sweat.

3. The method according to claim 1, wherein said at least one liquid sample is from human blood.

4. The method according to claim 1, wherein said cell structures are part of the hematological antigen system.

5. The method according to claim 1, wherein said cell structures are part of the antigens involved in HIV infection or detection.

6. The method according to claim 1, wherein said at least one liquid sample is from human blood and is used for the determination of circulating antibodies directed against bacteria, viruses or small sized single or multi cell infectious agents.

7. The method according to claim 1, wherein said at least one liquid sample is from human bone marrow.

8. The method according to claim 1, wherein said affinity binding means is selected from at least one of an antibody, an aptamer, a receptor, a ligand, a single chain antibody, a fragmented antibody and a lectin.

9. The method according to claim 1, wherein said cell structures are bound to said at least one retaining zone prior to said liquid sample adding step.

10. The method according to claim 1, including a first liquid adding step and a second liquid adding step, in which cell structures are bound following said first liquid adding step and said antibodies are bound following said second liquid adding step.

* * * * *